United States Patent
Takahashi et al.

(10) Patent No.: US 10,398,365 B2
(45) Date of Patent: Sep. 3, 2019

(54) FLUORESCENCE SENSOR

(71) Applicant: TERUMO KABUSHIKI KAISHA, Shibuya-ku, Tokyo (JP)

(72) Inventors: Masayuki Takahashi, Tokyo (JP); Hiroya Sato, Tokyo (JP); Eiji Arita, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 442 days.

(21) Appl. No.: 15/270,415

(22) Filed: Sep. 20, 2016

(65) Prior Publication Data
US 2017/0007163 A1 Jan. 12, 2017

Related U.S. Application Data

(63) Continuation of application No. PCT/JP2015/056068, filed on Mar. 2, 2015.

(30) Foreign Application Priority Data

Mar. 28, 2014 (JP) .................. 2014-069531

(51) Int. Cl.
*A61B 5/1459* (2006.01)
*G01N 21/64* (2006.01)
(Continued)

(52) U.S. Cl.
CPC .......... *A61B 5/1459* (2013.01); *A61B 5/0071* (2013.01); *A61B 5/1495* (2013.01);
(Continued)

(58) Field of Classification Search
CPC . A61B 5/0071; A61B 5/1455; A61B 5/14551; A61B 5/14552; A61B 5/14532;
(Continued)

(56) References Cited

U.S. PATENT DOCUMENTS

| 4,891,519 A | 1/1990 | Nohira et al. |
| 4,994,396 A | 2/1991 | Lefkowitz et al. |

(Continued)

FOREIGN PATENT DOCUMENTS

| DE | 197 19 422 A1 | 11/1998 |
| JP | 2001-513350 A | 9/2001 |

(Continued)

OTHER PUBLICATIONS

Office Action (Communication pursuant to Article 94(3) EPC) dated Apr. 16, 2018, by the European Patent Office in corresponding European Patent Application No. 15 768 688.2-1020. (9 pages).

(Continued)

*Primary Examiner* — Eric F Winakur
*Assistant Examiner* — Chu Chuan Liu
(74) *Attorney, Agent, or Firm* — Buchanan Ingersoll & Rooney PC

(57) ABSTRACT

A light guide unit of a fluorescence sensor is disclosed, which includes at least an optical-waveguide film in which one or more optical waveguides are formed. Each of these films includes a plurality of optical channels that output excitation light (E) or input fluorescence (F). All the optical channels are covered with a fluorescence unit.

14 Claims, 17 Drawing Sheets

(51) Int. Cl.
*G01N 21/77* (2006.01)
*A61B 5/00* (2006.01)
*A61B 5/1495* (2006.01)
*G01N 21/85* (2006.01)
*A61B 5/1455* (2006.01)

(52) U.S. Cl.
CPC ....... *G01N 21/645* (2013.01); *G01N 21/6486* (2013.01); *G01N 21/7703* (2013.01); *G01N 21/8507* (2013.01); *A61B 5/14551* (2013.01); *A61B 2562/0238* (2013.01); *A61B 2562/0242* (2013.01); *G01N 2021/6484* (2013.01); *G01N 2021/772* (2013.01); *G01N 2021/7723* (2013.01); *G01N 2021/7786* (2013.01); *G01N 2201/08* (2013.01)

(58) Field of Classification Search
CPC ........................................ A61B 5/1459; A61B 5/1495; G01N 21/7703; G01N 21/645; G01N 2201/7786; G01N 2201/772; G01N 2201/08; G01N 2201/6484; G01N 21/6486; G01N 2201/7723
See application file for complete search history.

(56) References Cited

U.S. PATENT DOCUMENTS

| | | | | |
|---|---|---|---|---|
| 5,001,054 | A * | 3/1991 | Wagner | A61B 5/14532 422/82.06 |
| 5,745,231 | A | 4/1998 | Groger et al. | |
| 6,584,335 | B1 | 6/2003 | Haar et al. | |
| 7,277,740 | B2 * | 10/2007 | Rohleder | A61B 5/14532 600/316 |
| 8,224,410 | B2 * | 7/2012 | Hadvary | A61B 5/14514 600/310 |
| 2002/0164547 | A1 | 11/2002 | Ferm et al. | |
| 2005/0113658 | A1 * | 5/2005 | Jacobson | A61B 5/14532 600/342 |
| 2006/0175555 | A1 | 8/2006 | Lau | |
| 2007/0251337 | A1 | 11/2007 | Reed et al. | |
| 2008/0146902 | A1 | 6/2008 | Hacker et al. | |
| 2010/0317949 | A1 | 12/2010 | Chamness et al. | |
| 2011/0245616 | A1 | 10/2011 | Kobayashi | |
| 2013/0060105 | A1 * | 3/2013 | Shah | A61B 5/6849 600/316 |

FOREIGN PATENT DOCUMENTS

| | | |
|---|---|---|
| JP | 2007-513333 A | 5/2007 |
| JP | 2010-160087 A | 7/2010 |
| WO | WO 2005/054831 A1 | 6/2005 |

OTHER PUBLICATIONS

International Search Report (PCT/ISA/210) dated May 26, 2015, by the Japanese Patent Office as the International Searching Authority for International Application No. PCT/JP2015/056068.
Anonymous: "Waveguide (optics)—Wikipedia, the free encyclopedia", Jul. 5, 2013, XP055410779, Retrieved from the Internet: URL:https://web.archive.org/web/20130705191632/https://en.wikipedia.org/wiki/Waveguide_(optics) (4 pages).
International Search Report (Form PCT/ISA/210) and the Written Opinion (Form PCT/ISA/237) dated May 26, 2015, in the corresponding International Application No. PCT/JP2015/056068. (12 pages).
International Preliminary Report on Patentability (Form PCT/IB/373) dated Oct. 4, 2016, in the corresponding International Application No. PCT/JP2015/056068. (1 page).
Extended European Search Report dated Oct. 16, 2017, issued by the European Patent Office in corresponding European Application No. 15768688.2. (12 pages).

* cited by examiner

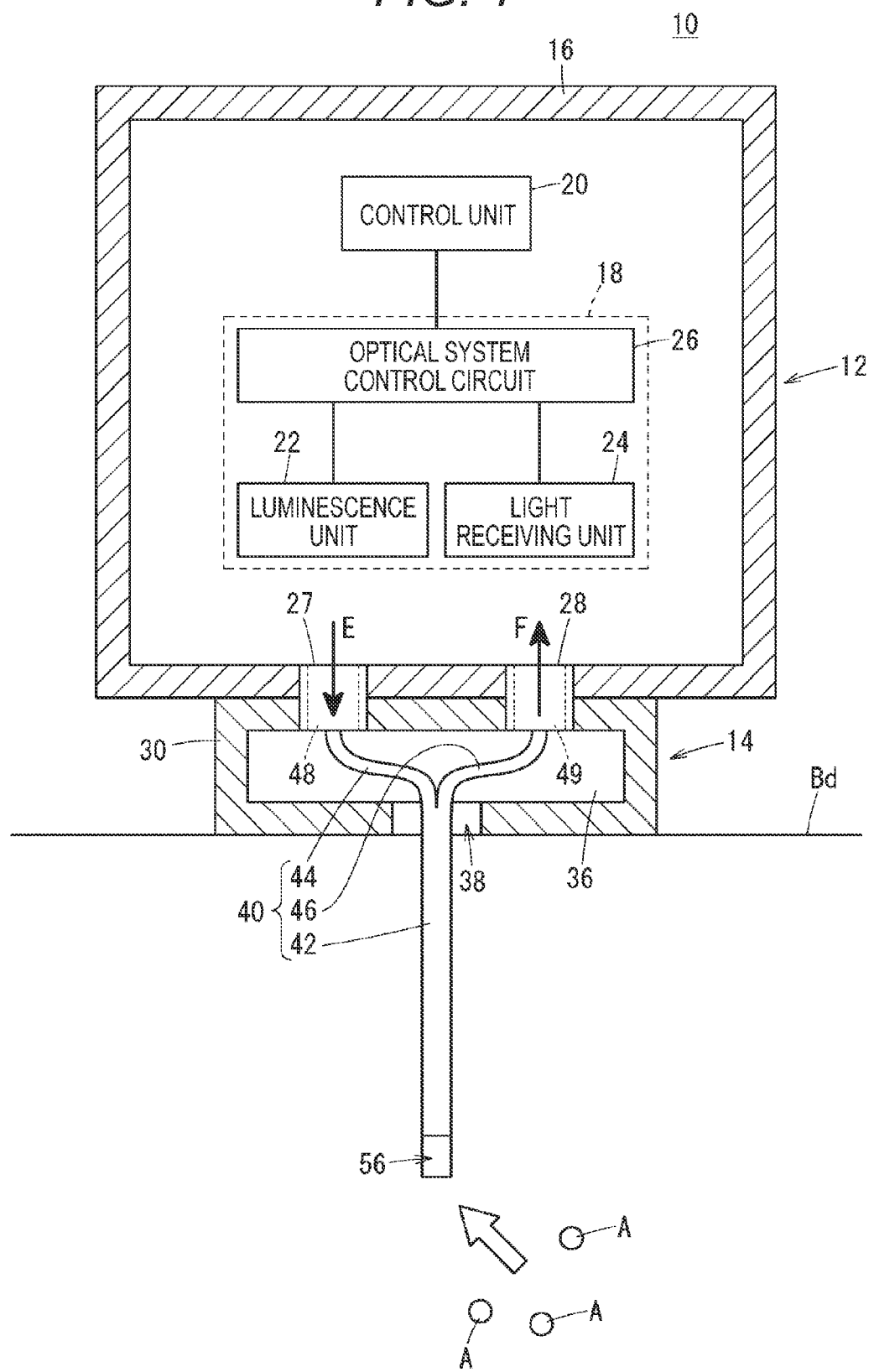

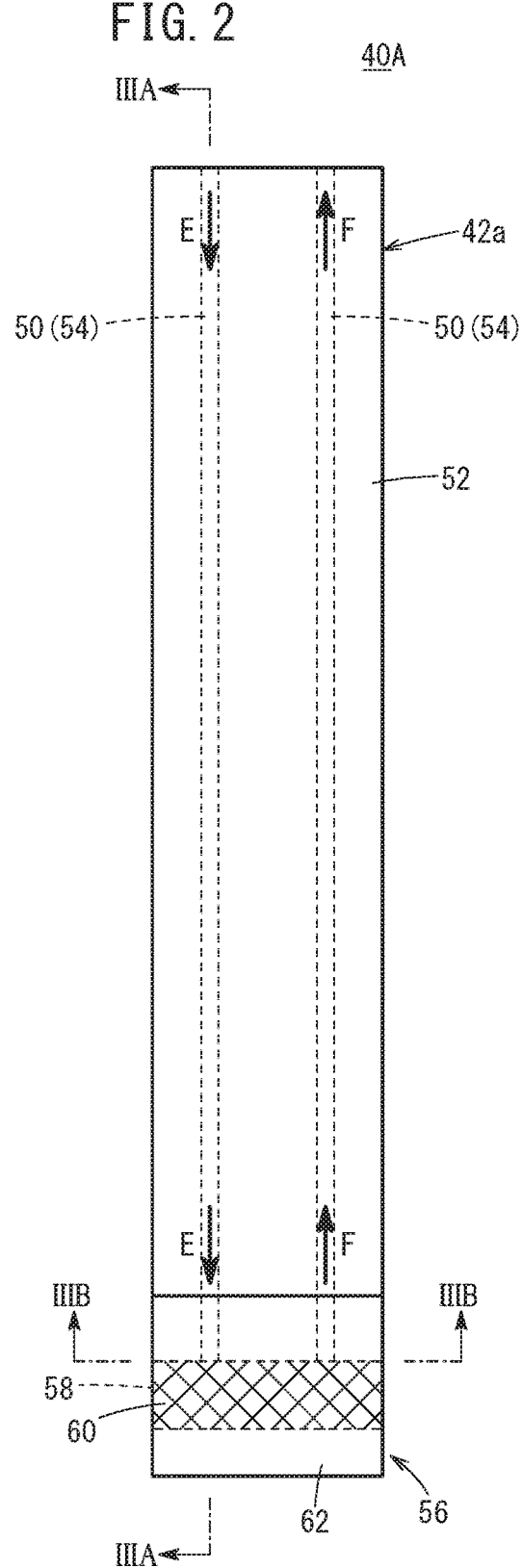

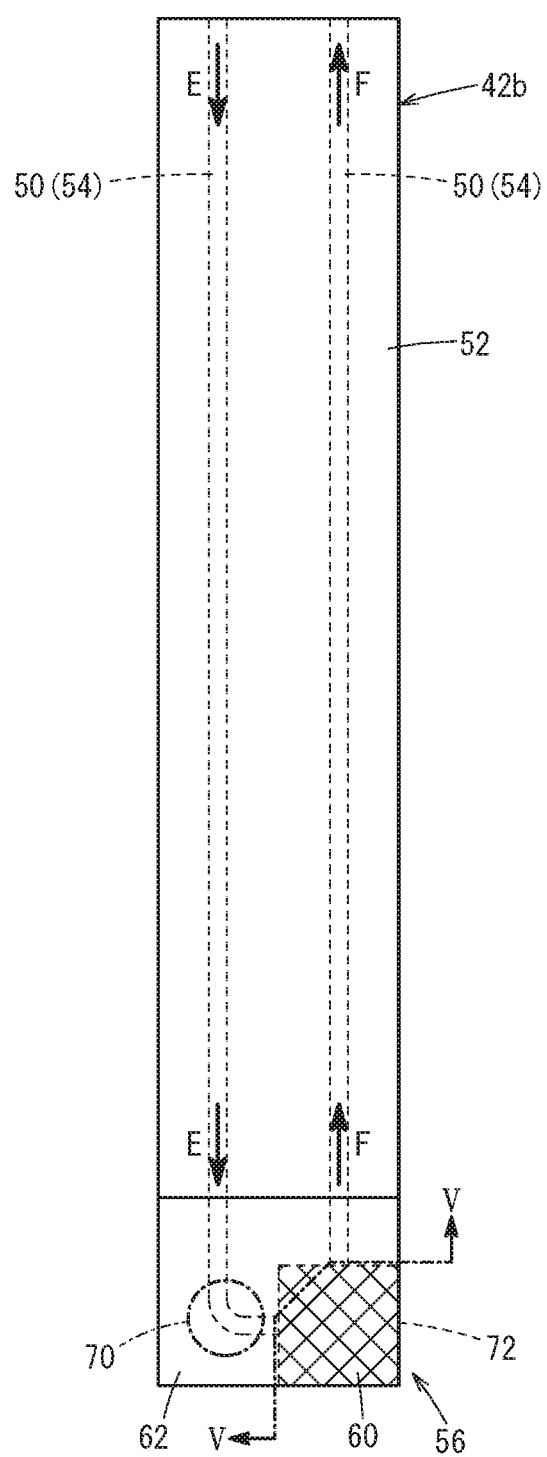

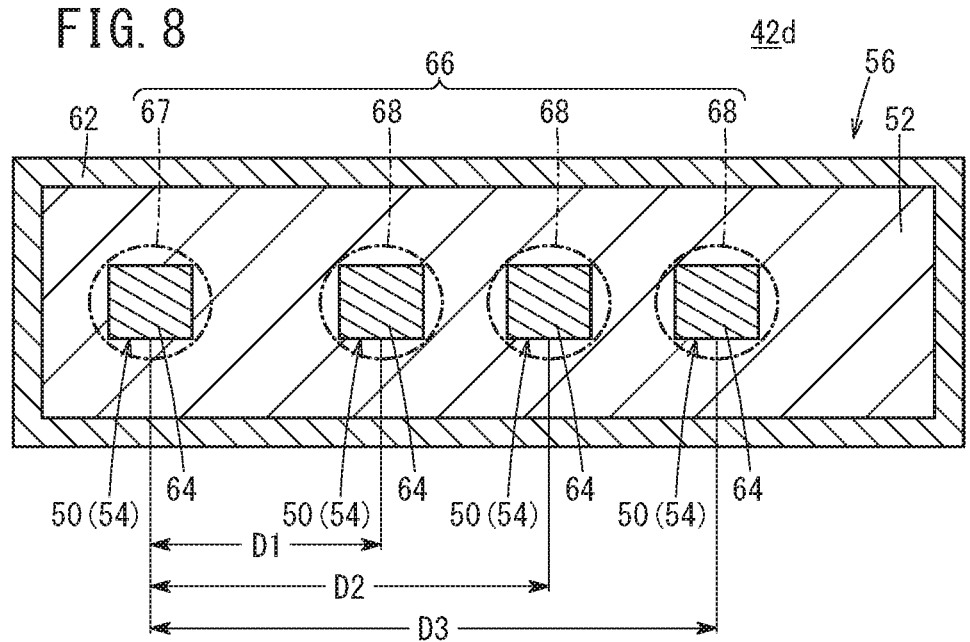

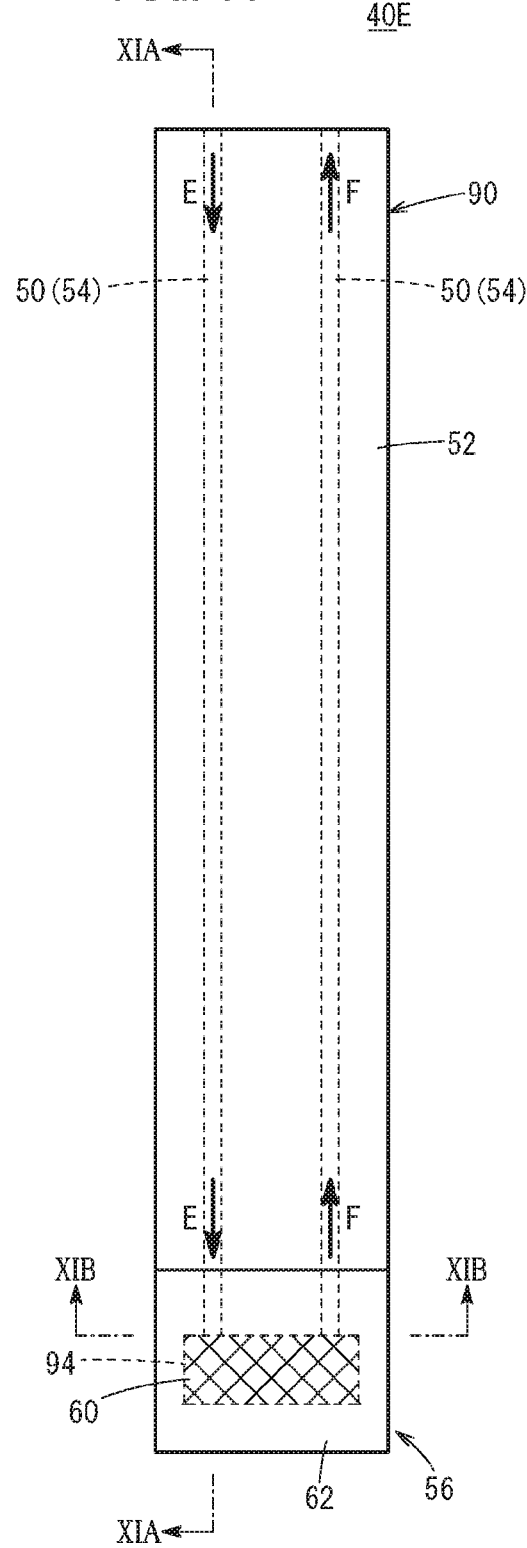

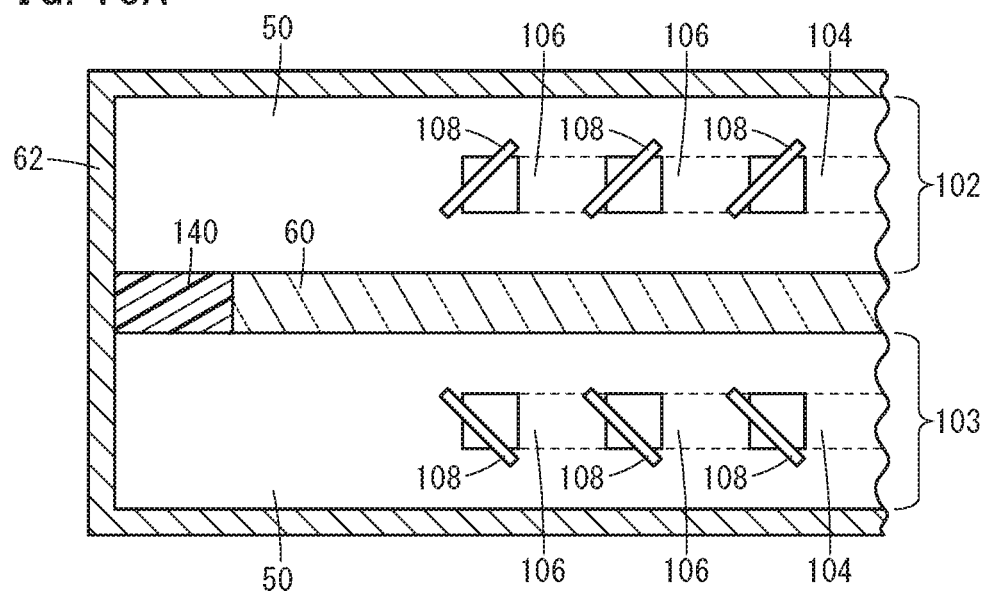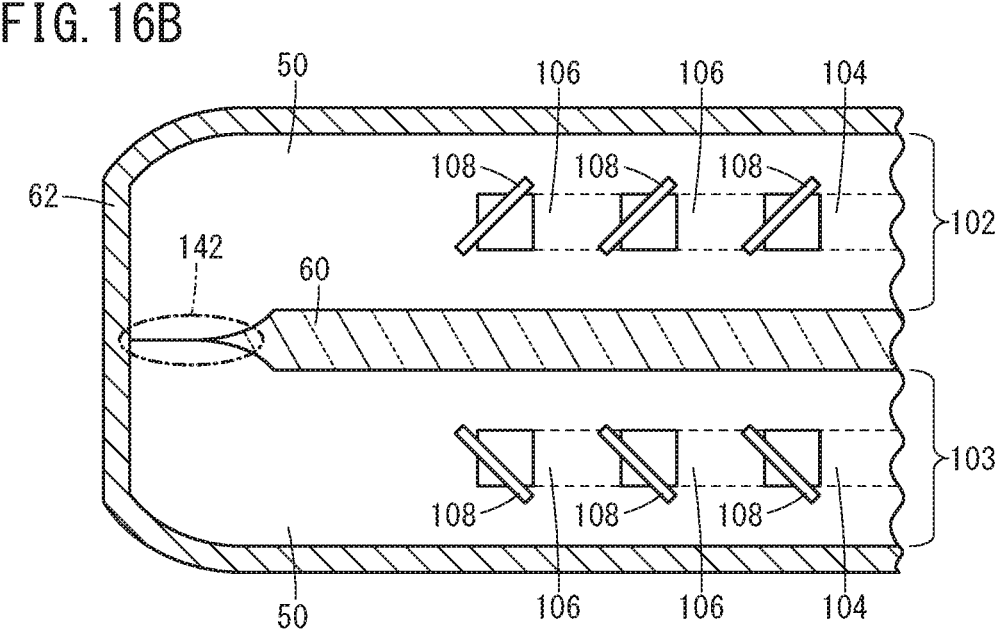

FLUORESCENCE SENSOR

CROSS-REFERENCES TO RELATED APPLICATIONS

This application is a continuation of International Application No. PCT/JP2015/056068 filed on Mar. 2, 2015, which claims priority to Japanese Application No. 2014-069531 filed on Mar. 28, 2014, the entire contents of both which are incorporated herein by reference.

TECHNICAL FIELD

The present disclosure relates to a fluorescence sensor including a fluorescence unit that generates fluorescence in the amount correlating with the concentration of analytes by receiving excitation light, and a measurement optical system that emits the excitation light and detects the fluorescence from the fluorescence unit.

BACKGROUND DISCUSSION

Fluorescence sensors that determine the concentration of analytes using the characteristics of the fluorescence that the fluorescence intensity varies depending on the interaction between the analyte and a marker substance are known. For example, an apparatus that determines the concentration of glucose while the whole or a part of the apparatus is embedded in the body of the test subject has been proposed.

Japanese PCT National Publication No. 2007-513333 describes a device in which an optical conduit (for example, a bifurcated fiber bundle) is provided in a puncture needle and a sensing element (for example, a fluorescence unit) is attached to the periphery of the distal end of the optical conduit. Japanese PCT National Publication No. 2007-513333 describes that excitation light is transmitted from the first fiber of the bifurcated fiber bundle and fluorescence is transmitted from the second fiber.

Such a type of fluorescence sensors has the design constraint that the sensing unit needs to be placed in or near the needle tip. Thus, it is necessary to increase the usage efficiency of the excitation light and the fluorescence while minimizing the size of the fluorescence unit. However, Japanese PCT National Publication No. 2007-513333 merely describes a schematic exemplary design and does not describe a specific configuration to increase the usage efficiency of the excitation light and the fluorescence.

SUMMARY

In light of the foregoing, a fluorescence sensor is disclosed that can simultaneously reduce the size of the sensing unit and improve the usage efficiency of the excitation light and the fluorescence.

A fluorescence sensor is disclosed, which includes a fluorescence unit that generates fluorescence in an amount correlating with concentration of analytes by receiving excitation light, a measurement optical system that emits the excitation light and detects the fluorescence from the fluorescence unit, a sensor body in which the measurement optical system is embedded, a light guide unit that is optically connected to the sensor body and bi-directionally guides light between the measurement optical system and the fluorescence unit, wherein the light guide unit includes at least an optical-waveguide film on which one or more optical waveguides are formed, the optical-waveguide film includes a plurality of optical channels that output the excitation light or input the fluorescence, and all the optical channels are covered with the fluorescence unit.

As described above, a light guide unit including at least an optical-waveguide film on which one or more optical waveguides are formed is provided and all the optical channels included in each optical-waveguide film are covered with the fluorescence unit. This can help prevent the light loss near the optical channels. This can simultaneously help improve the efficiency of usage of the excitation light and the fluorescence and downsize the sensing unit.

Furthermore, preferably, the light guide unit includes the optical-waveguide film on which the optical waveguides are formed, an exposure space used to expose end surfaces of the optical waveguides to an outside is formed on the optical-waveguide film, and all the optical channels are covered with the fluorescence unit inserted in the exposure space. This can form the light guide unit with the minimum number of optical-waveguide films, and thus can help reduce the size and cost of the apparatus.

Furthermore, preferably, the number of second channels that are the optical channels through which the fluorescence is input is larger than the number of first channels that are the optical channels through which the excitation light is output. The increase in the number of the second channels increases the amount of collectable light of the fluorescence.

Furthermore, preferably, the number of the first channels is one and the number of the second channels is two or more. Minimizing the number of first channels reduces the total number of optical waveguides. This can help save the space in the width direction of the optical-waveguide film.

Furthermore, preferably, the two or more second channels are at different distances from the first channel. Simultaneously obtaining different amounts of fluorescence depending on the distance between the optical channels can analyze the analytes from diversified perspectives.

Furthermore, preferably, directions of normal lines of the end surfaces of the second channels are perpendicular to a direction of a normal line of the end surface of the first channel. This helps make the rectilinear component of the excitation light from the first channel easy to reach the periphery of the second channel. Thus, the efficiency of collection of light of the fluorescence can be improved.

Furthermore, preferably, the light guide unit includes a film-layered unit in which two or more optical-waveguide films are layered and the one or more optical waveguides are formed on the two or more optical-waveguide films, an exposure space used to expose the end surfaces of the optical waveguides to an outside is formed on the film-layered unit, and all the optical channels are covered with the fluorescence unit inserted in the exposure space. This can help increase the number of optical channels with an extremely simple configuration.

Furthermore, preferably, the light guide unit includes a first optical-waveguide film and a second optical-waveguide film, the optical waveguide including a plurality of end units being formed on each of the first optical-waveguide film and the second optical-waveguide film, the first optical-waveguide film includes a plurality of first mirrors placed on the end units and configured to reflect the excitation light passing along the optical waveguide to the optical channels, the second optical-waveguide film includes a plurality of second mirrors placed on the end units and configured to reflect the fluorescence from the optical channels to the optical waveguide, and all the optical channels are covered with the fluorescence unit held between the first optical-waveguide film and the second optical-waveguide film. This can arrange many optical channels in the planar direction of the optical-waveguide film. Thus, the thickness of the fluorescence unit can be thinned.

Furthermore, preferably, positions of the first mirror and the second mirror facing each other are deviated from each other in a range in which relative positional difference or angular difference between the first mirror and the second mirror does not exceed a threshold. This can simultaneously help prevent the excitation light from entering through the optical channel of the second optical-waveguide film and maintain the efficiency of collection of light of the fluorescence. Thus, the degradation of the accuracy of determination of the analytes can be prevented.

Furthermore, preferably, the light guide unit includes an optical filter existing between the first mirror and the second mirror facing each other and having filter characteristics of allowing the fluorescence in a relatively large amount to pass through the optical filter and allowing the excitation light in a relatively small amount to pass through the optical filter. This can simultaneously help prevent the excitation light from entering through the optical channel of the second optical-waveguide film and maintain the efficiency of collection of light of the fluorescence, and thus can prevent the degradation of the accuracy of determination of the analytes.

Furthermore, preferably, the fluorescence unit includes fluorescent hydrogel. Using a fluorescence hydrogel with high viscosity increases the adhesion of the fluorescence unit with the optical channels. Thus, the efficiency of collection of light of the excitation light and fluorescence can be improved.

In the fluorescence sensor according to the present invention, a light guide unit including at least an optical-waveguide film on which one or more optical waveguides are formed is provided and all the optical channels included in each optical-waveguide film are covered with the fluorescence unit. This can drastically prevent the light loss near the optical channels. This can simultaneously help improve the efficiency of usage of the excitation light and the fluorescence and reduce the size of the sensing unit.

BRIEF DESCRIPTION OF THE DRAWINGS

FIG. 1 is a view of the whole configuration of a fluorescence sensor common among all the embodiments.

FIG. 2 is a front view of an optical-waveguide film included as a part of a light guide unit according to a first embodiment.

FIG. 4 is a front view of an optical-waveguide film included as a part of a light guide unit according to a first exemplary variation.

FIG. 8 is a cross-sectional view taken along line VIII-VIII of FIG. 7.

FIG. 10 is a front view of a film-layered unit included as a part of a light guide unit according to a second embodiment.

FIGS. 16A and 16B are schematic views of a process for manufacturing the light guide unit in the third embodiment.

DETAILED DESCRIPTION

Figure 3A:
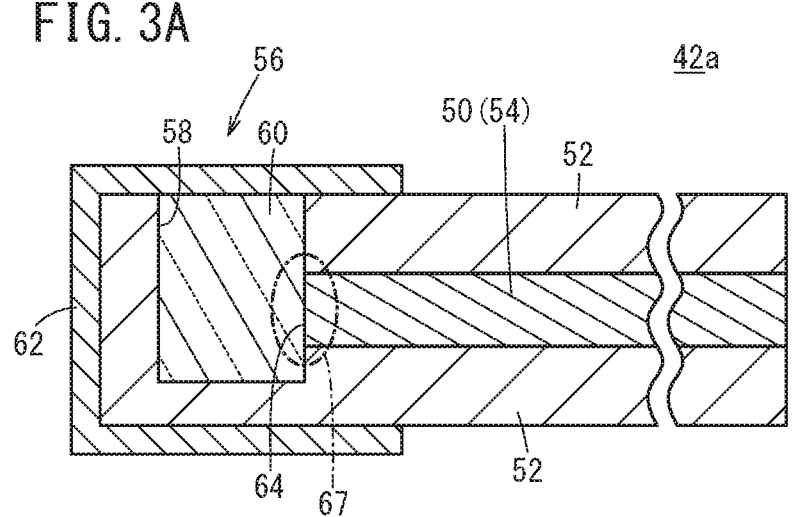
FIG. 3A is a cross-sectional view taken along line IIIA-IIIA of FIG. 2.

Hereinafter, the preferred embodiments of a fluorescence sensor according to the present invention will be described in detail with reference to the appended drawings.

FIG. 1 is a view of a configuration of a fluorescence sensor 10 common among all the embodiments. The fluorescence sensor 10 continuously or intermittently determines the concentration of analytes A while the fluorescence sensor 10 is implanted in the body of a test subject Bd. The fluorescence sensor 10 can include a roughly cuboid-shaped sensor body 12, and a measurement chip 14 attached to the sensor body 12.

A measurement optical system 18 that emits excitation light E and detects fluorescence F, and a control unit 20 that controls each unit of the sensor body 12 (including the measurement optical system 18) are embedded in a casing 16 of the sensor body 12.

The measurement optical system 18 can include a luminescence unit 22 that emits the excitation light E, a light receiving unit 24 that detects the fluorescence F generated in accordance with the excitation light E, and an optical system control circuit 26 that controls the drive of the luminescence unit 22 and the light receiving unit 24.

The luminescence unit 22 can include one or more luminescence elements. Various luminescence elements, including, for example, a light emitting diode (LED) device, an organic electro-luminescence (EL) device, an inorganic EL device, and a laser diode (LD) device can be used as the luminescence unit 22.

The light receiving unit 24 can include one or more light receiving elements. Various light receiving elements including, for example, a Photo Diode (PD) device, a photo conductor, and a Photo Transistor (PT) can be used as the light receiving unit 24.

The casing 16 can include two body-side connectors 27 and 28 to guide the excitation light E through the body-side connector 27 to the outside of the casing 16 and guide the fluorescence F through the body-side connector 28 into the casing 16.

The measurement chip 14 can include a roughly disk-shaped body 30, and a light guide unit 40 extending over an inside 36 and an opening 38 of the body 30. The light guide unit 40 bi-directionally guides light between the measurement optical system 18 and a fluorescence unit 60 (see FIG. 2 and FIG. 3A).

The light guide unit 40 can include an optical-waveguide group 42, a light-emitting-side light guide unit 44 branching from the optical-waveguide group 42 in one direction, and a light-receiving-side light guide unit 46 branching in another direction. Note that a chip-side connector 48 that can optically be connected to the body-side connector 27 is provided on the front side of the light-emitting-side light guide unit 44. Similarly, a chip-side connector 49 that can optically be connected to the body-side connector 28 is provided on the front side of the light-receiving-side light guide unit 46.

Figure 3B:
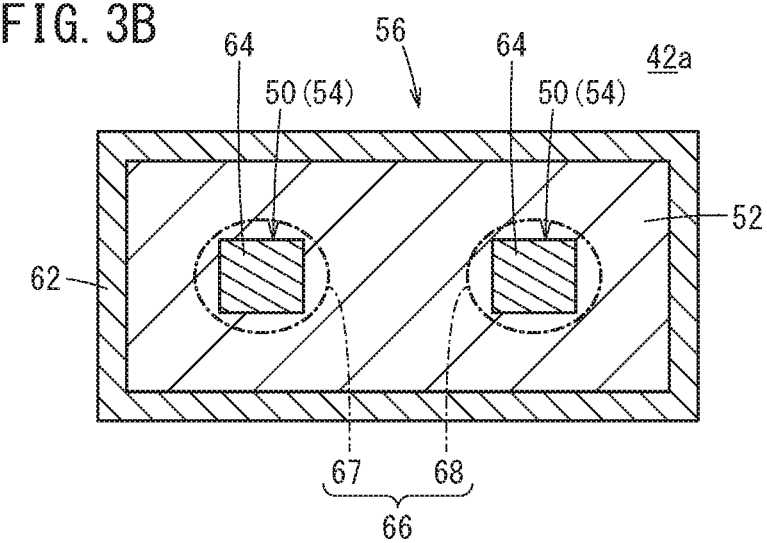
FIG. 3B is a cross-sectional view taken along line IIIB-IIIB of FIG. 2.

First, a light guide unit 40A according to the first embodiment will be described with reference to FIGS. 2 to 3B. Note that the optical-waveguide group 42 (FIG. 1) in the first embodiment (including the exemplary variations) is formed by an optical-waveguide film.

FIG. 2 is a front view of an optical-waveguide film 42a included as a part of the light guide unit 40A according to the first embodiment. FIG. 3A is a cross-sectional view taken along line IIIA-IIIA of FIG. 2. FIG. 3B is a cross-sectional view taken along line IIIB-IIIB of FIG. 2.

As illustrated in FIG. 2, the belt-shaped optical-waveguide film 42a can include a plurality of (two in the example of the drawing) linear cores 50, and a cladding portion 52 existing around the cores 50. The cladding portion 52 is made of a material with a lower optical refraction index than the optical refraction index of the cores 50. This causes the cores 50 to function as transmission paths (hereinafter, referred to as optical waveguides 54) through which excitation light E and the fluorescence F are transmitted. A first (left) one of the two optical waveguides 54 extending in parallel corresponds to the optical waveguide 54 of the excitation light E, and a second (right) one corresponds to the optical waveguide 54 of the fluorescence F. Note that the front unit 56 of the optical-waveguide film 42a is placed in the test subject Bd (FIG. 1).

As illustrated in FIGS. 2 and 3A, a cuboid-shaped concave portion 58 extending over the whole width of the optical-waveguide film 42a is formed on the front unit 56. A fluorescence unit 60 that works as an indicator is inserted into the concave portion 58. Furthermore, a light blocking layer 62 covers the whole surface of the front unit 56 (including the exposed surface of the fluorescence unit 60).

The fluorescence unit 60 generates the fluorescence F in the amount correlating with the concentration of analytes A by receiving the excitation light E. The fluorescence unit 60 can be a material that generates the fluorescence F in accordance with the reaction between the analyte A and a marker substance (fluorescence dye), or can be a material that generates the fluorescence F in accordance with the reaction between a component other than the analyte A and a marker substance.

The light blocking layer 62 has characteristics of allowing the analytes A among the components in the test subject Bd to pass through the light blocking layer 62 and does not allow high polymers except for the analytes A to pass through the light blocking layer 62 (for example, permselectivity). In addition, the light blocking layer 62 helps prevent the excitation light E and the fluorescence F from leaking outside the front unit 56 and helps prevent external light from entering the front unit 56.

As described with reference to FIGS. 3A and 3B, the concave portion 58 functions as an exposure space used to expose end surfaces 64 of the optical waveguides 54 to the outside. For example, the optical-waveguide film 42a can include a plurality of optical channels 66 that output the excitation light E or input the fluorescence F. Hereinafter, the optical channel 66 that outputs the excitation light E is sometimes referred to as a "first channel 67" and the optical channel 66 that inputs the fluorescence F is sometimes referred to as a "second channel 68" for differentiation.

Next, the operation of the fluorescence sensor 10 using the light guide unit 40A according to the first embodiment will be described with reference to FIGS. 1 to 3B.

First, using a sensor insertion device (not illustrated), the light guide unit 40A of the measurement chip 14 is implanted into the test subject Bd. After that, the body-side connectors 27 and 28 are fitted with the chip-side connectors 48 and 49, respectively. This allows some of the analytes A existing in the test subject Bd to pass through the light blocking layer 62 of the front unit 56 and enter the fluorescence unit 60.

The measurement optical system 18 receives the instruction signals from the control unit 20 and starts the operation for determining the concentration of the analytes A. Specifically, the luminescence unit 22 emits the excitation light E in accordance with the control signal from the optical system control circuit 26.

The emitted excitation light E enters the fluorescence unit 60 through the body-side connector 27, the chip-side connector 48, the light-emitting-side light guide unit 44, the optical waveguide 54 (on the left side of FIG. 2) of the optical-waveguide film 42a, and the first channel 67. After receiving the excitation light E, the fluorescence unit 60 generates the fluorescence F in the amount correlating with the concentration of the analytes A.

In this embodiment, the fluorescence unit 60 is preferably made of fluorescent hydrogel. This is because using fluorescent hydrogel with high viscosity increases the adhesion of the fluorescence unit 60 to the optical channels 66, and the increase in adhesion improves the efficiency of the collection of light of the excitation light E and the fluorescence F.

The generated fluorescence F enters the casing 16 through the second channel 68, the optical waveguide 54 (on the right side of FIG. 2) of the optical-waveguide film 42a, the light-receiving-side light guide unit 46, the chip-side connector 49, and the body-side connector 28.

In accordance with an exemplary embodiment, the optical system control circuit 26 obtains the detection signal correlating with the amount of light of the fluorescence F by processing the analog signal output from the light receiving unit 24 sequentially in a logarithmic amplification process and an A/D conversion process. The control unit 20 determines the concentration of the analytes A with reference to a predetermined calibration curve (a characteristic curve showing the relationship between the detection signal and the concentration).

As described above, the fluorescence sensor 10 can include the fluorescence unit 60 that generates the fluorescence F in the amount correlating with the concentration of the analytes A by receiving the excitation light E, and the measurement optical system 18 that emits the excitation light E and detects the fluorescence F from the fluorescence unit 60. The fluorescence sensor 10 can include the sensor body 12 in which the measurement optical system 18 is embedded, and the light guide unit 40A that is optically connected to the sensor body 12 and bi-directionally guides light between the measurement optical system 18 and the fluorescence unit 60.

The light guide unit 40A can include an optical-waveguide film 42a in which a plurality of optical waveguides 54 is formed. The optical-waveguide film 42a can include a plurality of optical channels 66 that output the excitation light E or input the fluorescence F. Furthermore, all the optical channels 66 are covered with the fluorescence unit 60.

As described above, the light guide unit 40A including the optical-waveguide film 42a in which the optical waveguides 54 are formed is provided and all the optical channels 66 included in the optical-waveguide film 42a are covered with the fluorescence unit 60. This can help prevent the light loss near the optical channels 66, and simultaneously downsize the sensing unit and improve the efficiency of usage of the excitation light E and the fluorescence F.

Additionally, the concave portion 58 (exposure space) used to expose the end surfaces 64 of the optical waveguides 54 to the outside is formed on the optical-waveguide film 42a, and all the optical channels 66 are covered with the fluorescence unit 60 inserted in the concave portion 58. This can help minimize the number of optical-waveguide films 42a forming the light guide unit 40A, and thus can help reduce the size and cost of the apparatus.

Next, a light guide unit 40B according to a first exemplary variation of the first embodiment will be described with reference to FIGS. 4 and 5. Hereinafter, the same configurations in this exemplary variation and other embodiments as the configuration of the first embodiment will be put with the same reference signs and the descriptions will be omitted.

FIG. 4 is a front view of an optical-waveguide film 42b included as a part of a light guide unit 40B according to the first exemplary variation. FIG. 5 is a cross-sectional view taken along line V-V of FIG. 4.

As described in FIG. 4, a core 50 (optical waveguide 54) of the belt-shaped optical-waveguide film 42b has a different shape from the shape of the cores of the optical-waveguide film 42a of the first embodiment. Specifically, the left one of the two optical waveguides 54 of the optical-waveguide film 42b has a C-shaped curve 70 curving to the right in the front unit 56.

Figure 5:
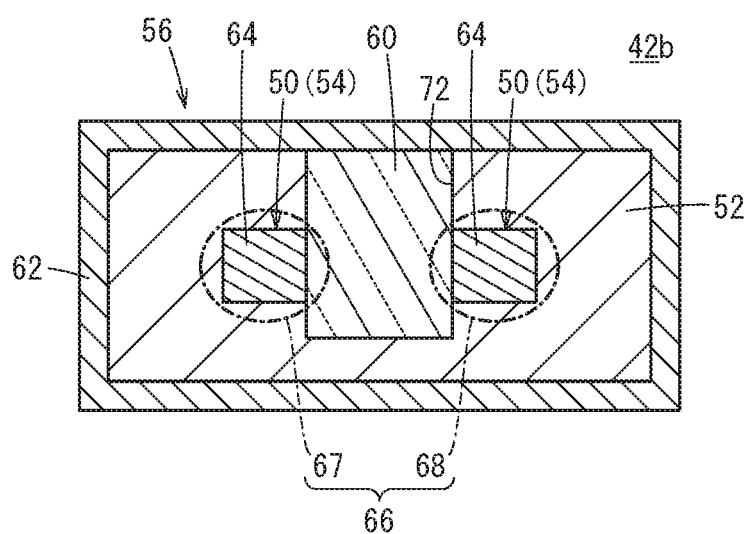
FIG. 5 is a cross-sectional view taken along line V-V of FIG. 4.

As illustrated in FIGS. 4 and 5, the right lower corner of the optical-waveguide film 42b is cut into a cuboid so that a cut portion 72 is formed in the front unit 56. The cut portion 72 is fully filled with the fluorescence unit 60. A light blocking layer 62 covers the whole surface of the front unit 56 (including the exposed surface of the fluorescence unit 60).

In this exemplary variation, the cut portion 72 functions as an exposure space used to expose the end surfaces 64 of the optical waveguides 54 to the outside. In accordance with an exemplary embodiment, for example, the optical-waveguide film 42b can include a plurality of optical channels 66 that output excitation light E or input the fluorescence F. The end surface 64 of a second channel 68 is roughly perpendicular to the end surface 64 of a first channel 67.

The configuration described above makes the rectilinear component of the excitation light E from the first channel 67 relatively easy to reach the periphery of the second channel 68. This helps improve the efficiency of collection of light of the fluorescence F. Note that the positional relationship between the end surface 64 of the second channel 68 and the end surface 64 of the first channel 67 is not limited to the relationship described above. Any relationship as long as the direction of the normal line of the end surface 64 of the second channel 68 crosses the direction of the normal line of the end surface 64 of the first channel 67 can bring about the same function effect as described above.

Figure 6:
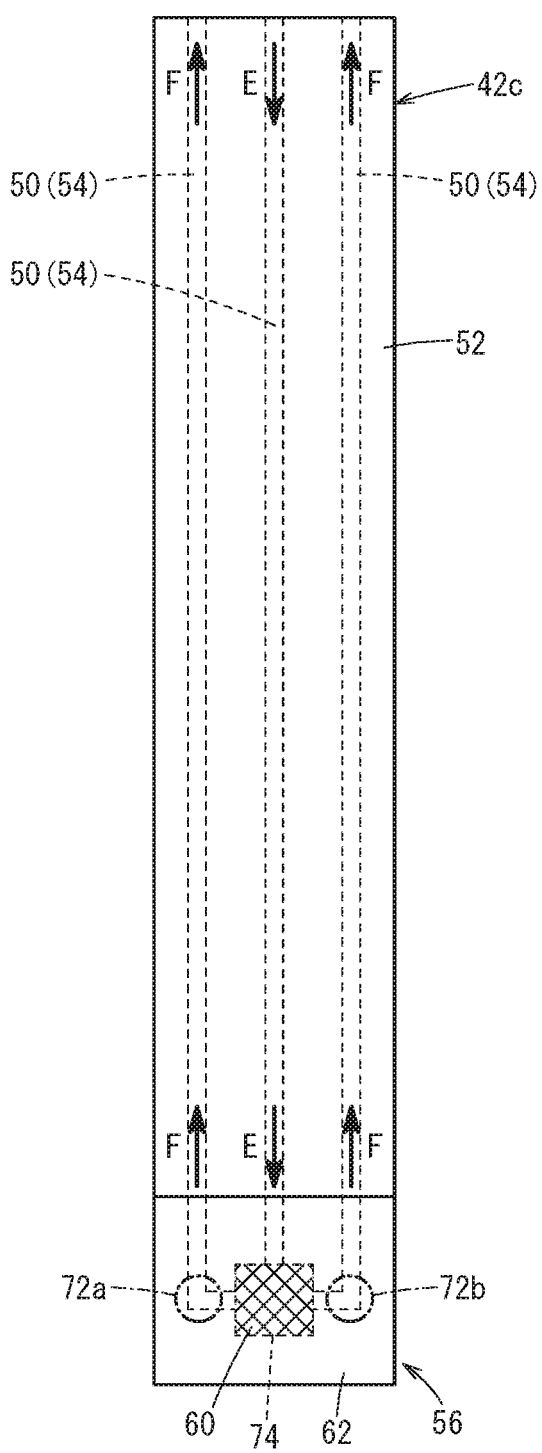
FIG. 6 is a front view of an optical-waveguide film included as a part of a light guide unit according to a second exemplary variation.

Next, a light guide unit 40C according to the second exemplary variation will be described with reference to FIG. 6. FIG. 6 is a front view of an optical-waveguide film 42c included as a part of the light guide unit 40C.

The number and shape of the cores 50 (the optical waveguides 54) of the belt-shaped optical-waveguide film 42c are different from the number and shape of the cores 50 of the optical-waveguide film 42a of the first embodiment. Specifically, three optical waveguides 54 are formed in parallel to each other on the base side of the optical-waveguide film 42c.

The leftmost optical waveguide 54 among the three optical waveguides 54 has an L-shaped bent portion 72a bent to the right in the front unit 56. The rightmost optical waveguide 54 among the three optical waveguides 54 has an L-shaped bent portion 72b bend to the left in the front unit 56. In this exemplary variation, the central optical waveguide 54 of the three optical waveguides 54 corresponds to the optical waveguide 54 of the excitation light E, and the other two optical waveguides 54 (on the right and left sides) correspond to the optical waveguides 54 of the fluorescence F.

A cuboid-shaped cavity 74 is formed roughly on the center of the front unit 56. The cavity 74 is fully filled with the fluorescence unit 60. The light blocking layer 62 covers the whole surface of the front unit 56 (including the exposed surface of the fluorescence unit 60).

In this exemplary variation, the cavity 74 functions as an exposure space used to expose the end surfaces 64 of the optical waveguides 54 to the outside. For example, the optical-waveguide film 42c can include a plurality of optical channels 66 that output the excitation light E or input the fluorescence F. The number of the second channels 68 is (two in the example of the drawing) larger than the number of the first channels 67 (one in the example of the drawing). In accordance with an exemplary embodiment, for example, the increase in the number of the second channels 68 increases the amount of collectable light of the fluorescence F.

Specifically, minimizing the number of first channels 67 (to one) reduces the total number of the optical waveguides 54, and thus can save the space in the width direction of the optical-waveguide film 42c.

Figure 7:
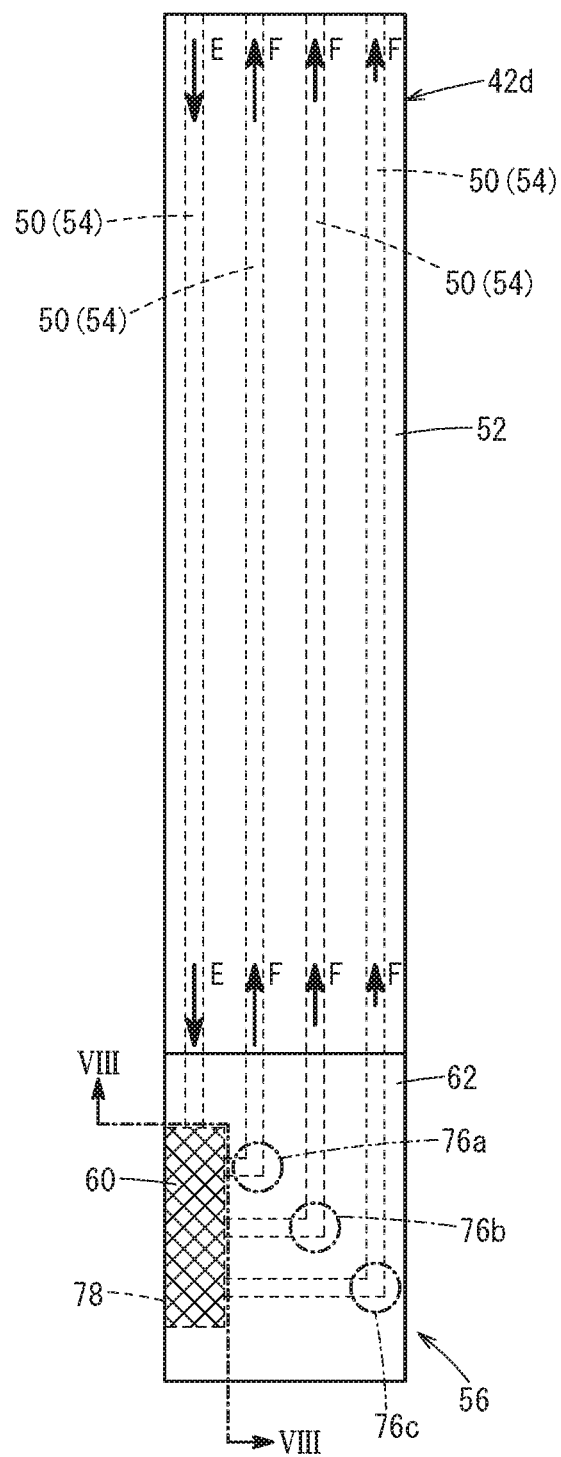
FIG. 7 is a front view of an optical-waveguide film included as a part of a light guide unit according to a third exemplary variation.

Next, a light guide unit 40D according to a third exemplary variation will be described with reference to FIGS. 7 to 9B. FIG. 7 is a front view of an optical-waveguide film 42d included as a part of the light guide unit 40D. FIG. 8 is a cross-sectional view taken along line VIII-VIII of FIG. 7.

As described FIG. 7, the number and shape of the cores 50 (the optical waveguides 54) of the belt-shaped optical-waveguide film 42d are different from the number and shape of the cores 50 of the optical-waveguide film 42a of the first embodiment. Specifically, four optical waveguides 54 are formed in parallel each other on the base side of the optical-waveguide film 42d.

The three optical waveguides 54 except for the leftmost optical waveguide 54 of the four optical waveguides 54 have L-shaped bent portions 76a, 76b, and 76c bent to the left in the front unit 56, respectively. In this exemplary variation, the leftmost one of the four optical waveguides 54 corresponds to the optical waveguide 54 of the excitation light E, and the other three optical waveguides 54 correspond to the optical waveguides 54 of the fluorescence F.

As illustrated in FIGS. 7 and 8, a side of the front unit 56 in the direction in which the optical-waveguide film 42d extends is cut into a cuboid so that a cut portion 78 is formed in the front unit 56. The cut portion 78 is fully filled with the fluorescence unit 60. A light blocking layer 62 covers the whole surface of the front unit 56 (including the exposed surface of the fluorescence unit 60).

In this exemplary variation, the cut portion 78 functions as an exposure space used to expose the end surfaces 64 of the optical waveguides 54 to the outside. In accordance with an exemplary embodiment, the optical-waveguide film 42d can include a plurality of optical channels 66 that output excitation light E or input the fluorescence F. The number of first channels 67 is one and the number of second channels 68 is two or more (three in the example of the drawing). Additionally, the second channels 68 have different positional relationships with the first channel 67 while having distances D1, D2, and D3 away from the first channel 67, respectively.

Generally, the nearer to the light source of the excitation light E the position is in the fluorescence unit 60, the more the amount of light of the fluorescence F is generated. Meanwhile, the farther from the light source of the excitation light E the position is, the less the amount of light of the fluorescence F is generated. Similarly, the nearer to the position at which the fluorescence F is generated the second channel 68 is, the more the amount of light of the fluorescence F is guided to the second channel 68. Meanwhile, the farther from the position at which the fluorescence F is generated the second channel 68 is, the less the amount of light of the fluorescence F is guided to the second channel 68. In this exemplary variation, the different amounts of the fluorescence F depending on the distance between the optical channels 66 are simultaneously obtained with the phenomenon described above and used to measure the analytes A.

Figure 9A:
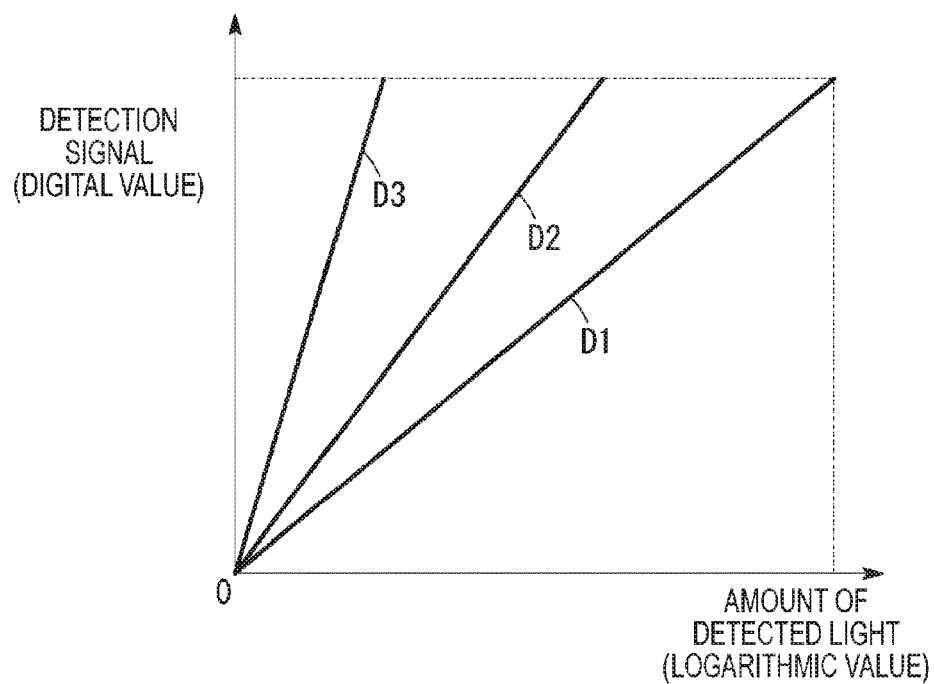
FIG. 9A is a view of a first conversion table when the optical-waveguide film of FIG. 7 is used.

FIG. 9A is a graph showing a first conversion table when the optical-waveguide film 42d of FIG. 7 is applied. The amount of detected light in the light receiving unit 24 (FIG. 1) is shown on the horizontal axis. The detection signal (digital value) output to the control unit 20 (in the same drawing) is shown on the vertical axis. In accordance with an exemplary embodiment, the first conversion table shows the conversion characteristic when the detected light is converted into a detection signal.

In the example of the drawing, the number of bits (the range of bits to be obtained) of the detection signal is fixed while the A/D resolutions in the distances D1 to D3 are different from each other. Specifically, the A/D resolution is the lowest in the shortest distance D1 and the A/D resolution is the highest in the longest distance D3.

Figure 9B:
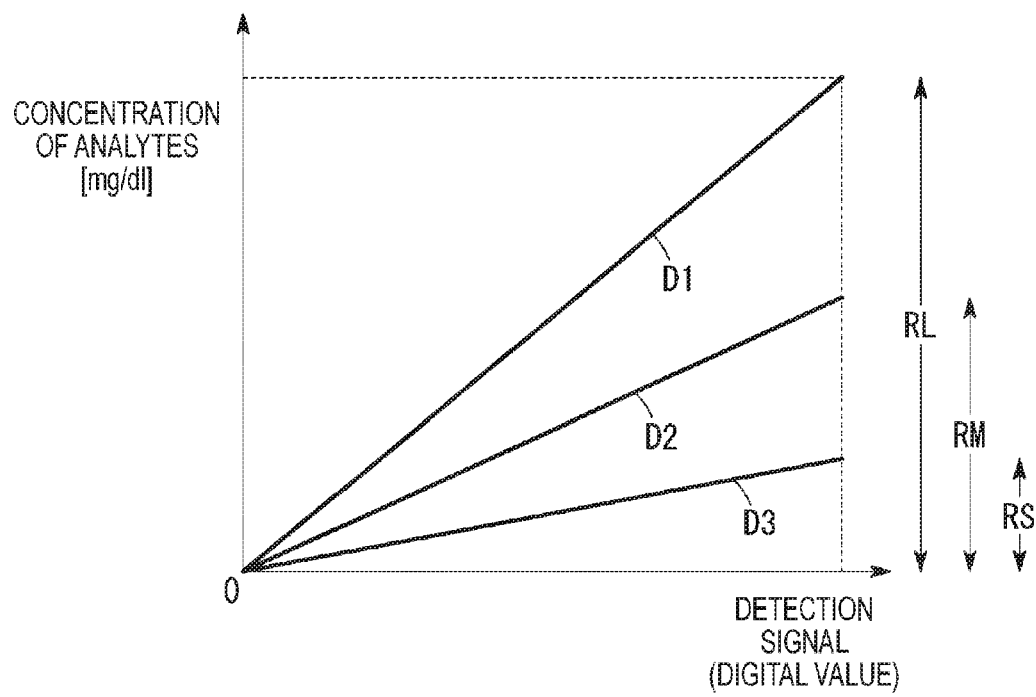
FIG. 9B is a view of a second conversion table when the optical-waveguide film of FIG. 7 is used.

FIG. 9B is a graph showing a second conversion table when the optical-waveguide film 42d of FIG. 7 is applied. The detection signal (digital value) is shown on the horizontal axis. The concentration (the unit is mg/dl) of the analytes A (FIG. 1) is shown on the vertical axis. In accordance with an exemplary embodiment, the second conversion table shows the conversion characteristic when the detected light is converted into the concentration.

In the example of the drawing, the number of bits (the range of bits to be obtained) of the detection signal is fixed while the concentration ranges (so called dynamic ranges) of the distances D1 to D3 are different from each other. Specifically, a dynamic range (RL) is the widest in the shortest distance D1 and a dynamic range (RS) is the narrowest in the longest distance D3.

The control unit 20 can determine the concentration of the analytes A by selectively using a plurality of calibration curves that are obtained by binding the first conversion table of FIG. 9A and the second conversion table of FIG. 9B. For example, using the detection signal and calibration curve in the distance D1 allows for the measurement of concentrations in a wide range (specifically, in a range of high concentrations). In accordance with an exemplary embodiment, for example, using the detection signal and calibration curve in the distance D3 allows for the measurement of concentrations in a range of low concentrations with high concentration resolution.

As described above, the two or more second channels 68 have different positional relationships with the first channel 67 while having distances D1 to D3 away from the first channel 67, respectively. The fluorescence F in different amounts depending on the distance between the optical channels 66 can simultaneously be obtained and the analytes A can be analyzed from diversified perspectives. As the example described above, the measurement can be performed in consideration of both the width of the dynamic range and the height of the concentration resolution.

Next, a light guide unit 40E according to a second embodiment will be described with reference to FIGS. 10 to 11B. Note that the optical-waveguide group 42 (FIG. 1) according to the second embodiment is formed by a plurality of layered optical-waveguide films (hereinafter, referred to as a film-layered unit) in this embodiment.

Figure 11A:
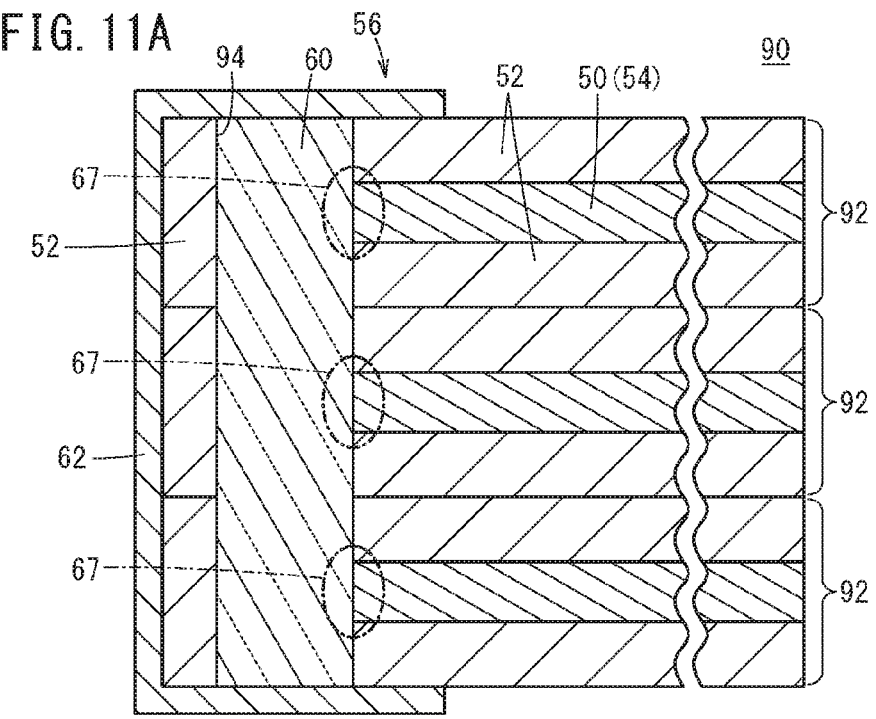
FIG. 11A is a cross-sectional view taken along line XIA-XIA of FIG. 10.

FIG. 10 is a front view of the film-layered unit 90 included as a part of the light guide unit 40E according to the second embodiment. FIG. 11A is a cross-sectional view taken along line XIA-XIA of FIG. 10. FIG. 11B is a cross-sectional view taken along line XIB-XIB of FIG. 10.

As described in FIGS. 10 and 11A, the belt-shaped film-layered unit 90 can include a plurality of (three in the example of the drawing) layered optical-waveguide films 92. Similarly to the optical-waveguide film 42a of FIG. 2, each optical-waveguide film 92 can include one or more (two in the example of the drawing) cores 50, and a cladding portion 52 existing around the cores 50. A first (left) one of the cores 50 corresponds to the optical waveguide 54 of the excitation light E and a second (right) one of the cores 50 corresponds to the optical waveguide 54 of the fluorescence F.

A cuboid-shaped opening 94 penetrating the film-layered units 90 in the thickness direction is formed roughly on the center of the front unit 56. The opening 94 is fully filled with the fluorescence unit 60. A light blocking layer 62 covers the whole surface of the front unit 56 (including the exposed surface of the fluorescence unit 60).

As described with reference to FIGS. 11A and 11B, the opening 94 functions as an exposure space used to expose the end surfaces 64 of the optical waveguides 54 to the outside. In accordance with an exemplary embodiment, for example, the film-layered units 90 include a plurality of optical channels 66 that output the excitation light E and input the fluorescence F.

Next, the operation of the fluorescence sensor 10 using the light guide unit 40E according to the second embodiment will be described with reference to FIGS. 1, and 10 to 11B. In this embodiment, only the points different from the first embodiment (the behavior of the light guide unit 40E) will be described.

Figure 11B:
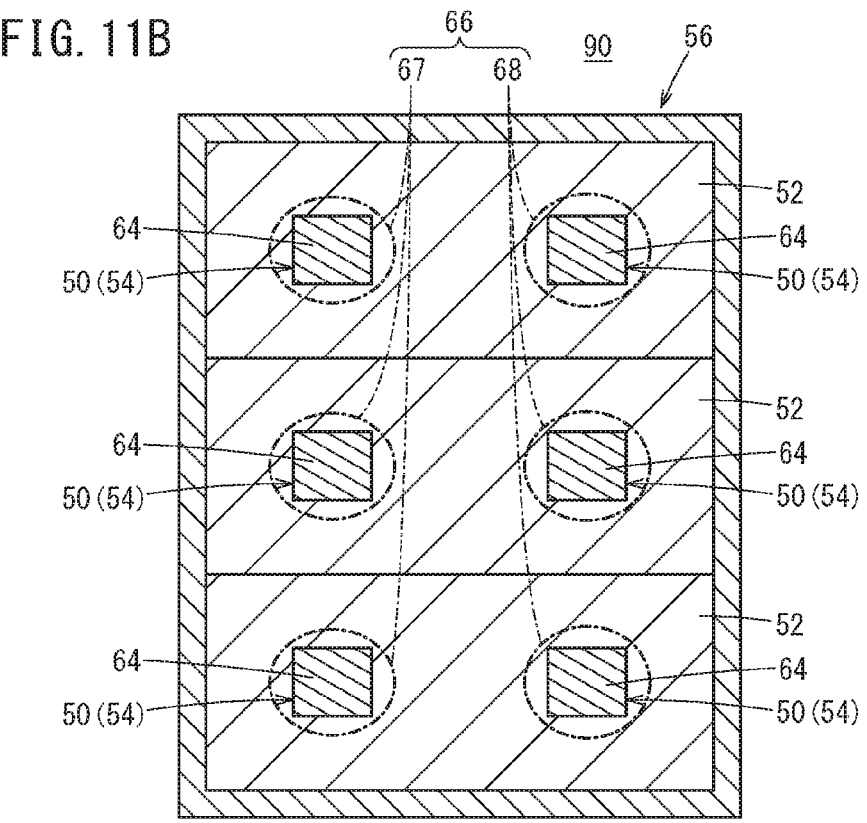
FIG. 11B is a cross-sectional view taken along line XIB-XIB of FIG. 10.

With reference to FIG. 1 again, the excitation light E enters the fluorescence unit 60 through the body-side connector 27, the chip-side connector 48, the light-emitting-side light guide unit 44, the optical waveguides 54 (on the left side of FIG. 10) of the optical-waveguide films 92, and the first channels 67 (three in the example of FIG. 11B). In this embodiment, the light-emitting-side light guide unit 44 functions as a light divider that divides the excitation light E in a transmission path into the three optical waveguides 54.

After that, the generated fluorescence F enters the casing 16 through the second channels 68 (three in the example of FIG. 11B), the optical waveguides 54 (on the right side of FIG. 10) of the optical-waveguide films 92, the light-receiving-side light guide unit 46, the chip-side connector 49, and the body-side connector 28. In this embodiment, the light-receiving-side light guide unit 46 functions as a light mixer that the fluorescence F in the three optical waveguides 54 into the transmission path.

As described above, the light guide unit 40E can include the film-layered unit 90 including two or more layered optical-waveguide films 92 in which one or more optical waveguides 54 are formed. An opening 94 (exposure space) used to expose the end surfaces 64 of the optical waveguides 54 to the outside is formed in the film-layered unit 90. Additionally, all the optical channels 66 are covered with the fluorescence unit 60 inserted in the opening 94.

The configuration described above can also bring about the same function effect as the first embodiment (the optical-waveguide film 42a). Thus, the number of optical channels 66 can be increased with an extremely simple configuration. Note that, although the three optical-waveguide films 92 are layered in FIGS. 11A and 11B, the number of optical-waveguide films 92 is not limited to the embodiment, and can be, for example, two, or four or more.

Next, a light guide unit 40F according to the third embodiment will be described with reference to FIGS. 12 to 13B. Note that the optical-waveguide group 42 (FIG. 1) according to the third embodiment is formed by two layered optical-waveguide films (a film-layered unit).

Figure 12:
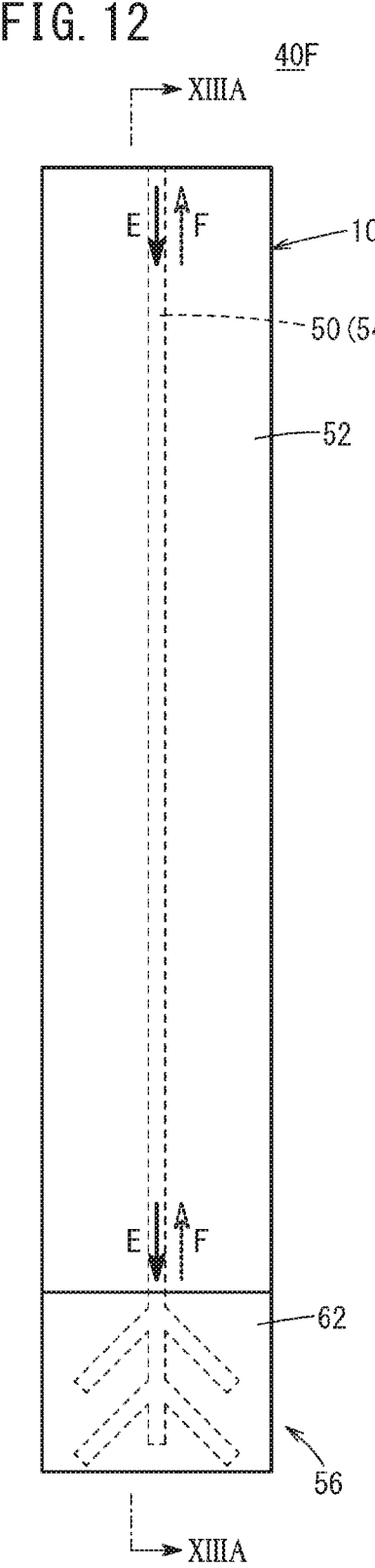
FIG. 12 is a front view of a film-layered unit included as a part of a light guide unit according to a third embodiment.
Figure 13A:
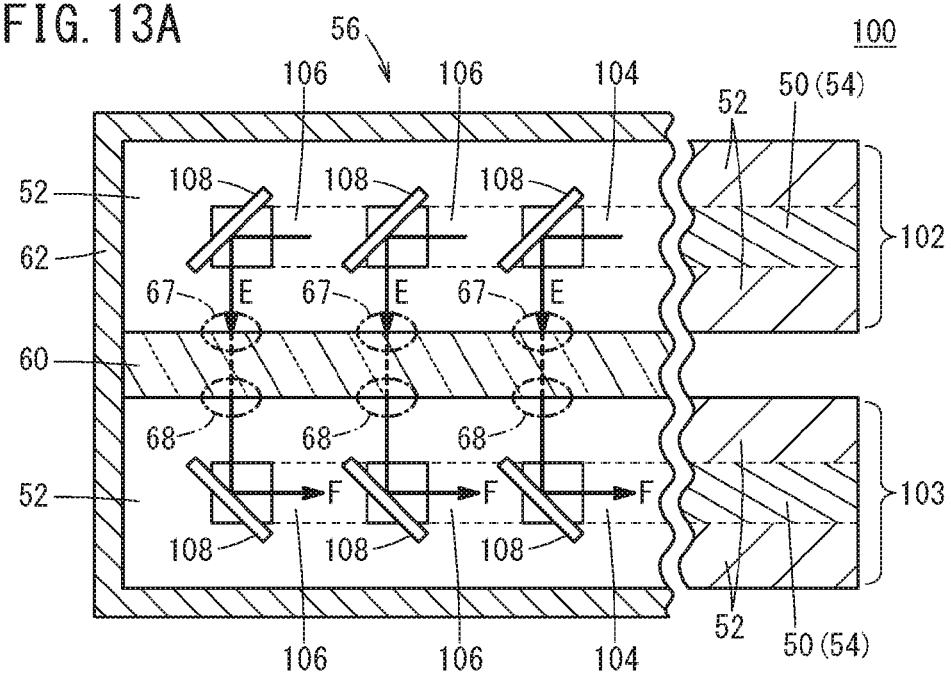
FIG. 13A is a cross-sectional view taken along line XIIIA-XIIIA of FIG. 12.

FIG. 12 is a front view of a film-layered unit 100 included as a part of the light guide unit 40F according to the third embodiment. FIG. 13A is a cross-sectional view taken along line XIIIA-XIIIA of FIG. 12. FIG. 13B is a schematic enlarged view of a part of the front unit 56 in FIG. 12.

As illustrated in FIGS. 12 and 13A, the belt-shaped film-layered unit 100 can include two layered optical-waveguide films 102 and 103. Each of the optical-waveguide films 102 and 103 can include a core 50 and a cladding portion 52 existing around the core 50. The core 50 of the optical-waveguide film 102 (the first optical-waveguide film) corresponds to the optical waveguide 54 of the excitation light E while the core 50 of the optical-waveguide film 103 (the second optical-waveguide film) corresponds to the optical waveguide 54 of the fluorescence F.

As illustrated in FIG. 13A, a fluorescence unit 60 is held between the two optical-waveguide films 102 and 103 in the front unit 56. A light blocking layer 62 covers the whole surface of the front unit 56 (including the exposed surface of the fluorescence unit 60).

Figure 13B:
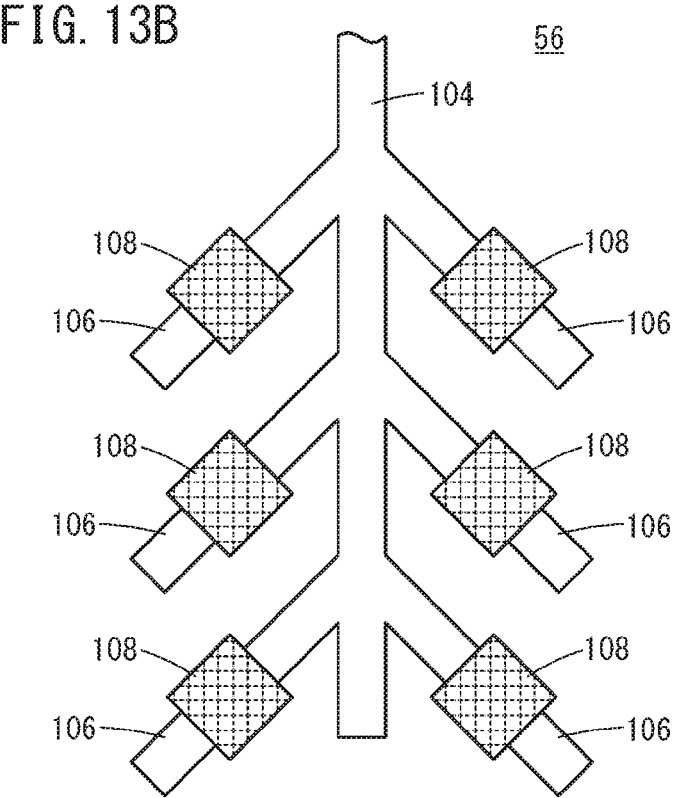
FIG. 13B is a schematic enlarged view of a part of a front portion of FIG. 12.

As illustrated in FIGS. 13A and 13B, the core 50 of the optical-waveguide film 102 can include a base unit 104, and a plurality of (three in the example of the drawing) end units 106 branching from the base unit 104. A plate-shaped mirror 108 is placed on each end unit 106. Each mirror 108 is inclined at a predetermined angle (approximately, 45 degrees) to the direction in which the end unit 106 extends and the direction of the normal line of the optical-waveguide film 102.

In accordance with an exemplary embodiment, the core 50 of the optical-waveguide film 103 has almost the same shape as the shape of the core 50 of the optical-waveguide film 102. The optical-waveguide films 102 and 103 can be fixed so that the positions of all the mirrors 108 on the upper and lower sides are aligned with each other.

Next, the operation of the fluorescence sensor 10 using the light guide unit 40F according to the third embodiment will be described with reference to FIGS. 1, and 12 to 13B. Hereinafter, the points different from the first embodiment (the behavior of the light guide unit 40F) will be described.

With reference to FIG. 1 again, the excitation light E enters the optical waveguide 54 (the base unit 104 and the end units 106) of the optical-waveguide film 102 through the body-side connector 27, the chip-side connector 48, and the light-emitting-side light guide unit 44.

After that, the excitation light E passing through the end units 106 is vertically reflected on the mirrors 108 (the first mirror unit) on the optical-waveguide film 102, and is output to the outside in the direction of the normal line of the optical-waveguide film 102. In accordance with an exemplary embodiment, for example, the optical-waveguide film 102 can include as many first channels 67 as the number of mirrors 108.

Then, the fluorescence unit 60 receiving the excitation light E generates the fluorescence F in the amount correlating with the concentration of the analytes A. The fluorescence F enters in the normal line from the outside of the optical-waveguide film 103.

The fluorescence F from the outside is vertically reflected on the mirrors 108 (the second mirror unit) on the optical-waveguide film 103, and is input to the optical waveguides 54 (the end units 106) of the optical-waveguide film 103. In accordance with an exemplary embodiment, for example, the optical-waveguide film 103 can include as many second channels 68 as the number of the mirrors 108.

After that, the fluorescence F enters the casing 16 through the optical waveguides 54 (the end units 106 and the base unit 104) of the optical-waveguide film 103, the light-receiving-side light guide unit 46, the chip-side connector 49, and the body-side connector 28.

As described above, the light guide unit 40F can include the optical-waveguide films 102 and 103 on which the optical waveguides 54 including the end units 106 are formed. The optical-waveguide film 102 can include the mirrors 108 placed on the end units 106 and reflecting the excitation light E passing through the optical waveguide 54 to the first channel 67. The optical-waveguide film 103 can include the mirrors 108 placed on the end units 106 and reflecting the fluorescence F from the second channel 68 to the optical waveguide 54.

Then, all the optical channels 66 can be covered with the fluorescence unit 60 held between the optical-waveguide films 102 and 103. This can also bring about the same function effect as the first embodiment (the optical-waveguide film 42a). Additionally, many optical channels 66 can be placed in the planar direction of the optical-waveguide films 102 and 103. This can help reduce the thickness of the fluorescence unit 60.

Note that, although an optical waveguide 54 including the end units 106 is formed in each of the optical-waveguide films 102 and 103, two or more optical waveguides 54 can be formed.

In accordance with an exemplary embodiment, in the example of FIGS. 13A and 13B, the optical-waveguide films 102 and 103 can be fixed so that the positions of all the mirrors 108 on the upper and lower sides are aligned with each other. This alignment can sometimes cause the optical-waveguide film 103 to guide the light including not only the fluorescence F but also the excitation light E through the second channels 68. In accordance with an exemplary embodiment, for example, detecting the excitation light E that is a noise factor together with the fluorescence F may reduce the accuracy of the determination of the concentration of the analytes A. In light of the foregoing, various methods for simultaneously preventing the excitation light E from entering through the second channel 68 and maintaining the efficiency of collection of light of the fluorescence F can be adopted as improvement.

First, the method in which the light axes of a pair of mirrors 108 and 108 facing each other are deviated from each other can be considered. For example, the positions of the mirrors 108 and 108 of the pair can be deviated from each other in a range in which the relative positional difference does not exceed a threshold (for example, 10 µm, preferably 5 µm) in the planar view of the film-layered unit 100. Alternatively, the positions of the mirrors 108 and 108 of the pair can be deviated from each other in a range in which the relative angular difference does not exceed a threshold (for example, five degrees, preferably two degrees).

Second, a method in which at least an optical filter is put between a pair of mirrors 108 and 108 facing each other can be considered. This optical filter has the filter characteristics of allowing a relatively large amount of fluorescence F to pass through the optical filter and allowing a relatively small amount of excitation light E to pass through the optical filter. The filter characteristics can be any one of a low-pass filter, a high-pass filter, and a band-pass filter. In accordance with an exemplary embodiment, It is the most preferable to allow the whole fluorescence F to pass through the filter and block the whole excitation light E. Specifically, when the wave lengths of the excitation light E and the fluorescence F are peaked at, for example, 585 nm and 610 to 630 nm, respectively, an optical filter that allows only light with a wavelength band of 585 to 630 nm to pass through the optical filter can be used.

The optical filter can be made of a substrate material including glass or plastic and mixed with a light-absorbing material, or can be a substrate on which an optical thin film (in more detail, a metal thin film or a dielectric thin film) is formed.

Note that the optical filter can be placed in the optical-waveguide film 103 (each place between the second channel 68 and the mirror 108), or can be placed outside the optical-waveguide film 103 (each place between the first channel 67 and the second channel 68).

Next, an exemplary method for manufacturing the fluorescence sensor 10 (in more detail, the light guide units 40A to 40E) will be described with reference to FIGS. 14A to 15. Hereinafter, the method for manufacturing the light guide unit 40A will be mainly described.

(1) First, to prepare the light guide unit 40A (the optical-waveguide film 42a), an optical waveguide sheet 130 is manufactured. The layered film (namely, the light guide unit 40A) can be formed, for example, with 50 to 300 µm in thickness.

The optical waveguide sheet 130 can be manufactured, for example, with a photo-addressing method. In the photo-addressing method, a core layer is applied and formed on the substrate, and the core layer is irradiated with ultraviolet in a predetermined pattern using a photo mask and heated. This forms a part with a relatively high optical refraction index and a part with a relatively low optical refraction index in the core layer.

The core layer can be made, for example, of acrylic resin, epoxy resin, polyimide resin, benzocyclobutene resin, or cycloolefin resin such as norbornene resin. Materials of which optical refraction index varies by the irradiation with active energy ray or heat addition can include materials of which principal material is resin composition including benzocyclobutene resin, and cycloolefin resin including norbornene resin.

The material of which the cladding layer is made is not especially limited to a material as long as the material has a lower optical refraction index than the optical refraction index of the material of which the core is made. Specifically, acrylic resin, epoxy resin, polyimide resin, and cycloolefin resin such as norbornene resin can be cited as the material.

Figure 14A:
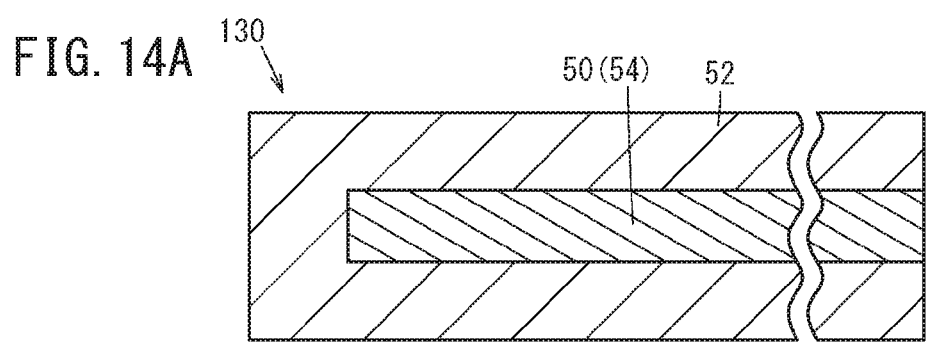
FIGS. 14A to 14D are schematic views of a process for manufacturing the light guide unit in the first and second embodiments.
Figure 14B:
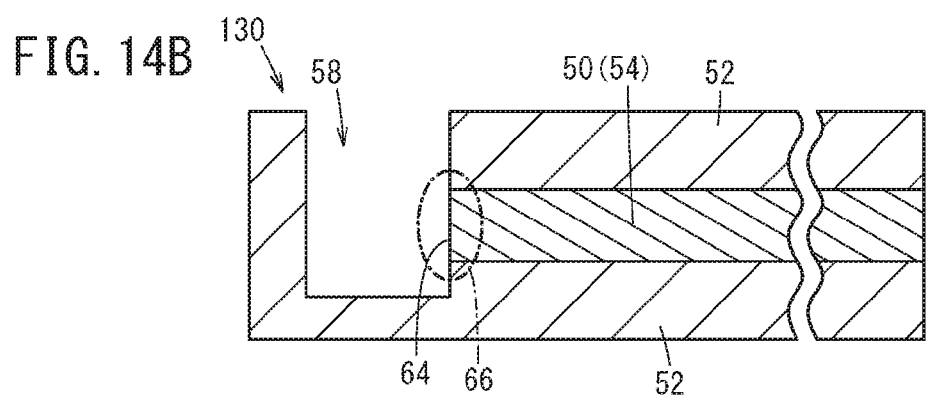
Figure 14C:
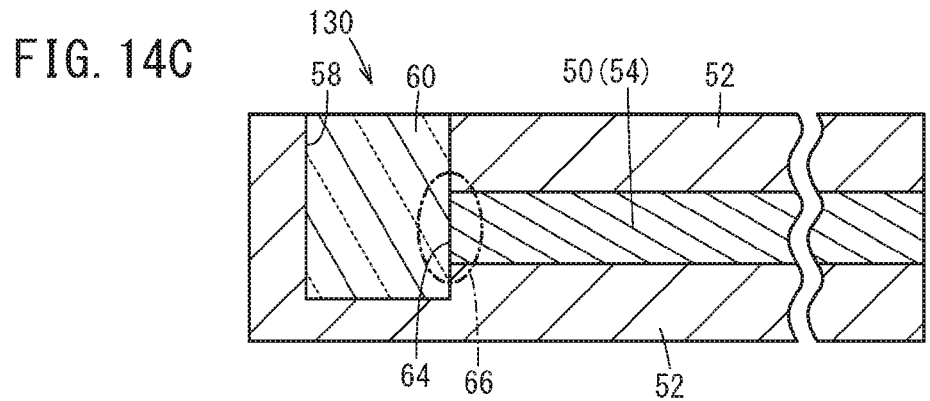

After that, forming a cladding layer on both sides of the core layer provides optical waveguide sheet 130 including linear cores 50 arranged at regular intervals (see FIG. 14A). In this example, the cores 50 are formed by the parts with a relatively high optical refraction index in the core layer. The cladding portion 52 is formed by the parts with a relatively low optical refraction index and the cladding layer in the core layer.

Note that the optical waveguide sheet 130 can be formed with a duplication method or a direct exposure method to be described below in replace of the photo-addressing method.

In the duplication method, a cladding layer is applied and formed on a substrate. Next, a transfer unit on which a plurality of protrusions corresponding to core patterns is pressed on the cladding layer so that the core patterns are transferred on the cladding layer. Next, a core material is injected into the core patterns (the concave portions) transferred on the cladding layer. After that, an upper cladding layer is formed on the formed cladding layer. This provides an optical waveguide sheet 130. In this method, the core material forms the core 50, and the cladding layer and the upper cladding layer form the cladding portion 52.

In the direct exposure method, a lower cladding layer is applied and formed on a substrate, and a core layer is applied and formed on the formed lower cladding layer. Next, the core layer is exposed to ultraviolet. Specifically, the core layer is irradiated with ultraviolet in a predetermined pattern using a photo mask. The core layer is partially removed while the core patterns remain. This forms a plurality of cores 50 on the lower cladding layer. After that, an upper cladding layer is formed on the lower cladding layer and the cores 50. This provides an optical waveguide sheet 130. In this method, the lower cladding layer and the upper cladding layer form the cladding portion 52.

Next, a groove is formed at a predetermined position on a first end of the optical waveguide sheet 130 (corresponding to the front unit 56) in the direction perpendicular to the direction in which the core 50 extends. The groove can be formed with various publicly known microfabrication technologies including cutting and laser irradiation. Forming the groove corresponding to the concave portion 58 exposes to the outside of the end surface 64 of each core 50 (see FIG. 14B).

Next, the groove formed on the optical waveguide sheet 130 is fully filled with the fluorescence unit 60. Specifically, a liquid material (a photo-curable material) is poured into the groove by capillary action, and then the groove is irradiated with active-energy light ray (for example, ultraviolet). Thus, the liquid material is gelled. The whole end surface 64 exposed to the outside is covered with the fluorescence unit 60 (see FIG. 14C).

The fluorescence dye included in the fluorescence unit 60 can be a material that is selected depending on the type of the analytes A and reversibly varies the amount of light of the fluorescence F generated depending on the amount of the analytes A. To measure sugar such as glucose, materials reversibly binding with glucose, such as ruthenium organic complexes, fluorescent phenylboronic acid derivatives, or fluorescein binding with protein can be used as the fluorescence dye.

Additionally, for example, to measure the hydrogen ion concentration or the carbon dioxide in the body of the test subject Bd, hydroxy pyrene trisulfonic acid derivatives can be used as the fluorescence dye. To measure the sugar in the body, phenylboronic acid derivatives bearing fluorescent residues can be used as the fluorescence dye. To measure the potassium ions in the body, crown ether derivatives bearing fluorescent residues can be used as the fluorescence dye.

In accordance with an exemplary embodiment, the fluorescence sensor 10 can be used for various purposes as an oxygen sensor, a glucose sensor, an pH sensor, an immune sensor, and a bacteriological sensor by selecting the fluorescence dye as described above.

Figure 14D:
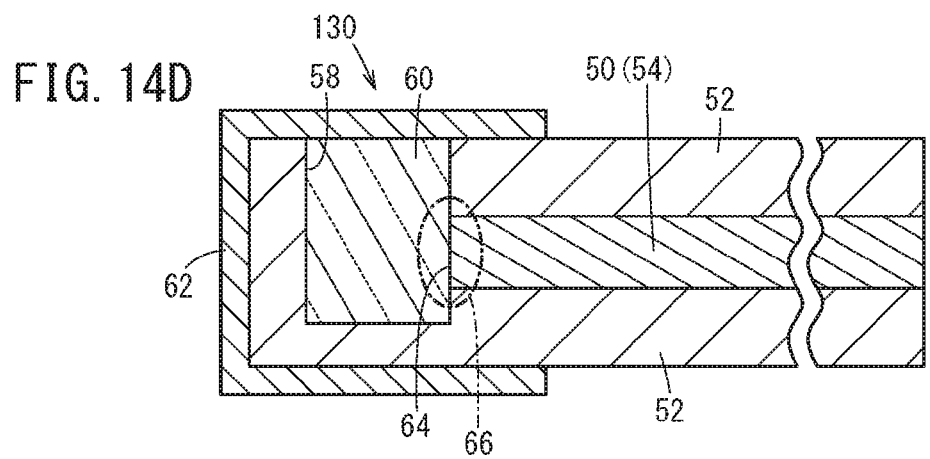

Next, a light blocking layer 62 is formed on a part of the optical waveguide sheet 130 so that the whole periphery of the fluorescence unit 60 is covered with the light blocking layer 62 (see FIG. 14D). The light blocking layer 62 is made of a material that has biocompatibility and does not block the flow of body fluid including the analytes A (for example, high-polymer gel). Then, mixing the high-polymer gel with particles that do not allow light to pass through the particles such as carbon black or carbon nanotube makes the light blocking layer 62 have both permselectivity and light-blocking effect.

Figure 15:
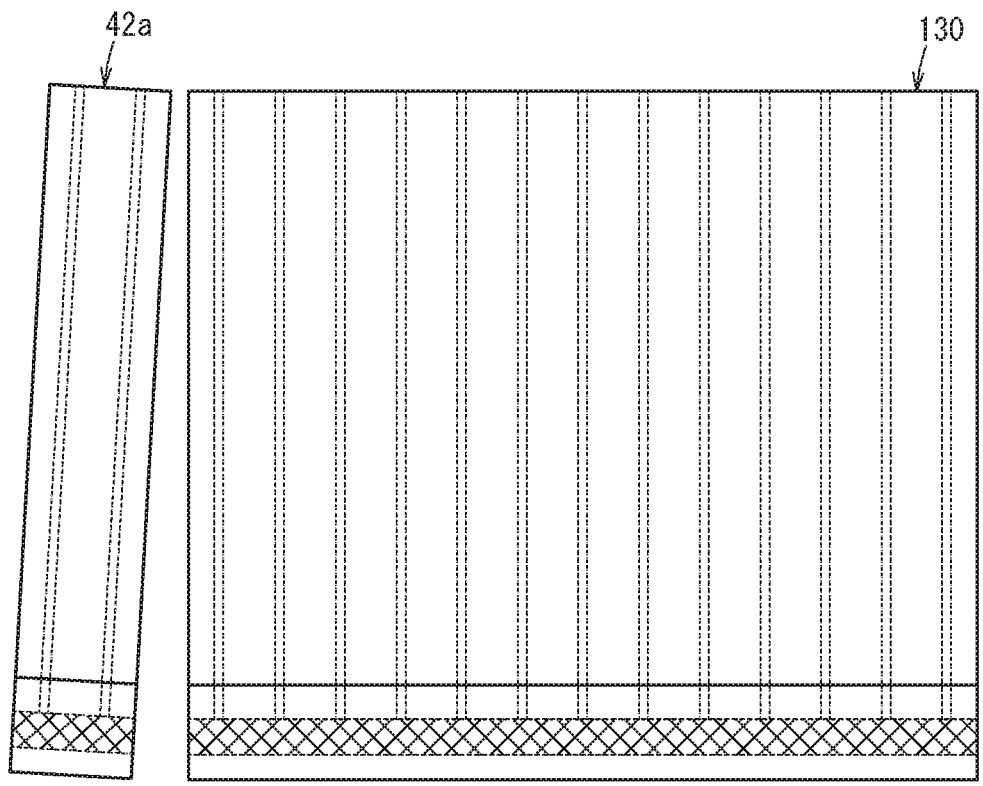
FIG. 15 is a schematic view of a process for manufacturing the light guide unit in the first and second embodiments.

Finally, the optical waveguide sheet 130 including the light blocking layer 62 is cut into rectangles in the direction in which the core 50 extends (see FIG. 15). This completes the light guide unit 40A (see FIGS. 2 to 3B). Note that the light guide units 40B to 40E can also be completed with the manufacturing methods described above.

Next, an exemplary method for manufacturing the light guide unit 40F will be described with reference to FIGS. 16A to 16B.

First, to prepare the light guide unit 40F (the film-layered unit 100), an optical waveguide sheet 130 is manufactured. Wood-like cores 50 are arranged at regular intervals, for example, many optical waveguides 54 including a plurality of end units 106 are formed on the optical waveguide sheet 130.

Next, flat mirrors 108 are formed on specific positions of the end units 106, respectively, with a photolithographic technology. Each mirror 108 has a size in which the cross-sectional surface of the core 50 is fully covered. To form the mirrors 108, for example, excimer laser or YAG laser can be used.

Next, the optical waveguide sheet 130 is cut into rectangles in the direction in which the core 50 extends. This forms two optical-waveguide films 102 and 103.

Next, the fluorescence unit 60 is put between the optical-waveguide films 102 and 103 and the optical-waveguide films 102 and 103 are fixed. As a method for fixing the optical-waveguide films 102 and 103, for example, a method in which the optical-waveguide films 102 and 103 are stuck to each other through an adhesion layer 140 (see FIG. 16A), or a method in which a contact part 142 where the optical-waveguide films 102 and 103 have contact with each other is welded by heat welding and ultrasonic welding (see FIG. 16B) are cited.

Finally, covering the whole periphery of the fluorescence unit 60 with a light blocking layer 62 completes the light guide unit 40F (see FIGS. 12 to 13B).

The present invention is not limited to the embodiments, and can be changed without departing the gist of the present invention.

Figure 17:
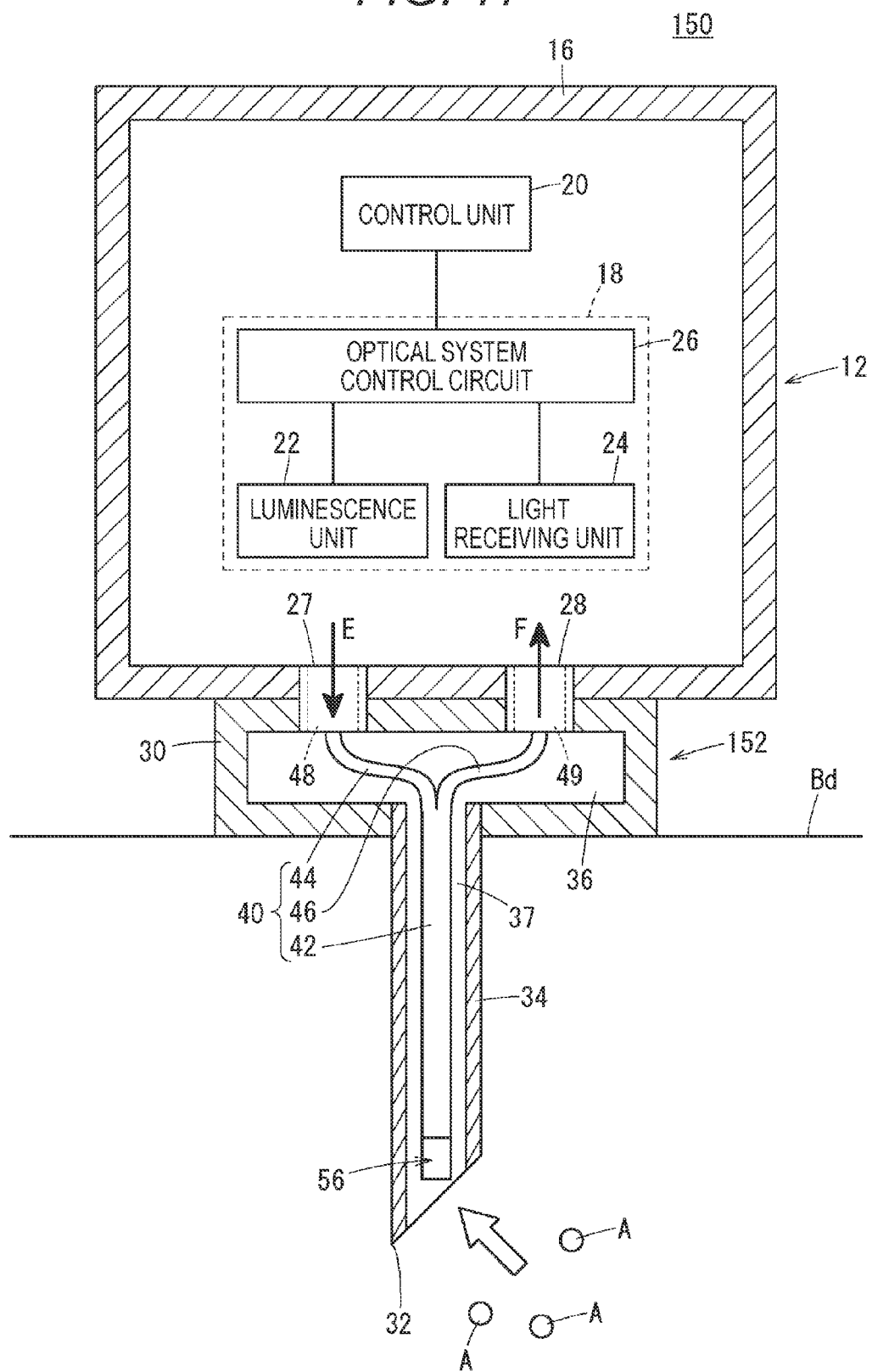
FIG. 17 is a view of the whole configuration of a fluorescence sensor according to another embodiment.

FIG. 17 is a view of the whole configuration of a fluorescence sensor 150 in another embodiment. The fluorescence sensor 150 is an apparatus that continuously or intermittently determines the concentration of analytes A while the fluorescence sensor 150 is inserted in the body of a test subject Bd. The fluorescence sensor 150 can include a sensor body 12, and a measurement chip 152 installed on the sensor body 12.

The measurement chip 152 can include a roughly disk-shaped body 30, a puncture needle 34 fixed on a principal surface of the body 30 and including the needle tip 32, and a light guide unit 40 extending over the inside 36 of the body 30 and the inside 37 of the puncture needle 34. In this embodiment, inserting the needle tip 32 in the test subject Bd allows for the installation of the fluorescence sensor 150 on the test subject Bd without another different device.

The detailed description above describes a fluorescence sensor. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A fluorescence sensor comprising:
a fluorescence unit configured to generate fluorescence in an amount correlating with a concentration of an analyte by receiving excitation light;
a measurement optical system configured to emit the excitation light and detects the fluorescence from the fluorescence unit;
a sensor body in which the measurement optical system is embedded;
a light guide unit configured to be optically connected to the sensor body and bi-directionally guides light between the measurement optical system and the fluorescence unit;
wherein the light guide unit includes at least an optical waveguide arrangement on which one or more optical waveguides are formed;
the optical waveguide arrangement includes a plurality of optical channels that output the excitation light or input the fluorescence;
each of the plurality of optical channels is covered with the fluorescence unit;
wherein the light guide unit includes a first optical-waveguide film and a second optical-waveguide film, the optical waveguide including a plurality of end units formed on each of the first optical-waveguide film and the second optical-waveguide film;
the first optical-waveguide film includes a plurality of first mirrors placed on the end units and configured to reflect the excitation light passing along the optical waveguide to the optical channels;
the second optical-waveguide film includes a plurality of second mirrors placed on the end units and configured to reflect the fluorescence from the optical channels to the optical waveguide; and each of the optical channels is covered with the fluorescence unit held between the first optical-waveguide film and the second optical-waveguide film.

2. The fluorescence sensor according to claim 1, wherein positions of the first mirror and the second mirror facing each other are deviated from each other in a range in which relative positional difference or angular difference between the first mirror and the second mirror does not exceed a threshold.

3. The fluorescence sensor according to claim 1, wherein the light guide unit includes an optical filter existing between the first mirror and the second mirror facing each other and having filter characteristics of allowing the fluorescence in a relatively large amount to pass through the optical filter and allowing the excitation light in a relatively small amount to pass through the optical filter.

4. The fluorescence sensor according to claim 1, wherein the fluorescence unit includes fluorescent hydrogel.

5. The fluorescence sensor according to claim 1, wherein the plurality of first mirrors and the plurality of second mirrors are plate-shaped mirrors.

6. The fluorescence sensor according to claim 5, wherein the plurality of first mirrors and the plurality of second mirrors are each inclined at a predetermined angle, the predetermined angle being 45 degrees.

7. The fluorescence sensor according to claim 1, further comprising:
a light blocking layer configured to cover an exposed surface of the fluorescence unit.

8. A fluorescence sensor comprising:
a fluorescence unit configured to generate fluorescence in an amount correlating with a concentration of an analyte by receiving excitation light;
a measurement optical system configured to emit the excitation light and detects the fluorescence from the fluorescence unit;
a sensor body in which the measurement optical system is embedded;
a light guide unit configured to be optically connected to the sensor body and bi-directionally guides light between the measurement optical system and the fluorescence unit, the light guide unit including at least an optical waveguide arrangement on which one or more optical waveguides are formed, the optical waveguide arrangement includes a plurality of optical channels that output the excitation light or input the fluorescence and wherein each of the plurality of optical channels are covered with the fluorescence unit;
wherein the light guide unit includes a first optical-waveguide film and a second optical-waveguide film, the optical waveguide including a plurality of end units formed on each of the first optical-waveguide film and the second optical-waveguide film;
the first optical-waveguide film includes a plurality of first mirrors placed on the end units and configured to reflect the excitation light passing along the optical waveguide to the optical channels;
the second optical-waveguide film includes a plurality of second mirrors placed on the end units and configured to reflect the fluorescence from the optical channels to the optical waveguide;
each of the optical channels is covered with the fluorescence unit held between the first optical-waveguide film and the second optical-waveguide film; and
a puncture needle having a needle tip, the puncture needle fixed on a surface of the body of sensor.

9. The fluorescence sensor according to claim 8, comprising:
a disk-shaped measurement chip installed on the sensor body, and wherein the puncture needle is fixed to a surface of the disk-shaped measurement chip.

10. The fluorescence sensor according to claim 8, wherein the needle tip is configured to be inserted into a living body, which allows installation of the fluorescence sensor on the living body without another device.

11. The fluorescence sensor according to claim 8, wherein positions of the first mirror and the second mirror facing each other are deviated from each other in a range in which relative positional difference or angular difference between the first mirror and the second mirror does not exceed a threshold.

12. The fluorescence sensor according to claim 8, wherein the plurality of first mirrors and the plurality of second mirrors are plate-shaped mirrors.

13. The fluorescence sensor according to claim 12, wherein the plurality of first mirrors and the plurality of second mirrors are each inclined at a predetermined angle, the predetermined angle being 45 degrees.

14. The fluorescence sensor according to claim 8, further comprising:
a light blocking layer configured to cover an exposed surface of the fluorescence unit.

* * * * *